United States Patent

Mueller

[11] 4,355,182
[45] Oct. 19, 1982

[54] HYDROXY-SUBSTITUTED PHOSPHORANES AND SALTS

[75] Inventor: Richard A. Mueller, Glencoe, Ill.

[73] Assignee: G.D. Searle & Co., Skokie, Ill.

[21] Appl. No.: 172,781

[22] Filed: Jul. 28, 1980

[51] Int. Cl.³ .............................. C07F 9/50; C07F 9/54
[52] U.S. Cl. ............................................ 568/11; 568/9
[58] Field of Search ...................................... 568/9, 11

[56] References Cited

U.S. PATENT DOCUMENTS 3,471,569 10/1969 Freipchlag et al. ................. 568/11

Primary Examiner—Helen M. S. Sneed
Attorney, Agent, or Firm—Albert Tockman; W. Dennis Drehkoff

[57] ABSTRACT

Hydroxy-substituted phosphoranes and salts thereof represented by Formulae I and II

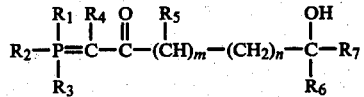

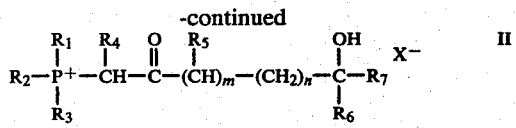

wherein $R_1$, $R_2$ and $R_3$ are the same or different members of the group consisting of lower alkyl, $C_5$-$C_6$ cycloalkyl, and

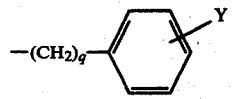

wherein q is an integer from 0 to 4 and Y is selected from the group consisting of hydrogen, halogen, lower alkyl and lower alkoxy; $R_4$ can be hydrogen or $C_1$-$C_3$ straight or branched chain alkyl; the sum of $n+m=3-5$; $R_5$ is hydrogen or lower alkyl; $R_6$ and $R_7$ are the same or different members of the group consisting of hydrogen, lower alkyl, and

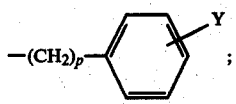

p is an integer of 0 or 1; and X is an anion.

The compounds are useful as intermediates for the heterocyclic phosphonium salts disclosed and claimed in U.S. Pat. No. 4,075,407. An improved process for preparing the phosphonium salts of U.S. Pat. No. 4,075,407 is also provided by the present invention.

26 Claims, No Drawings

HYDROXY-SUBSTITUTED PHOSPHORANES AND SALTS

BACKGROUND OF THE INVENTION

U.S. Pat. No. 4,075,407 disclosed and claims heterocyclic phosphonium salts represented by the formula

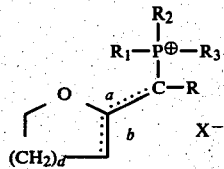

wherein d is 1, 2 or 3; R is hydrogen or $C_1$–$C_3$ alkyl; $R_1$, $R_2$ and $R_3$ each are $C_1$–$C_6$ alkyl, $C_5$–$C_6$ cycloalkyl or

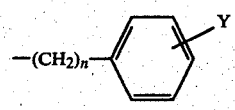

wherein n is 0–4 and Y is selected from the group consisting of hydrogen, halogen, $C_1$–$C_6$ alkyl, $C_1$–$C_6$ alkoxy; X is a pharmaceutically acceptable anion; and one of a and b is a double bond and the other is a single bond. The compounds are analgesic agents.

U.S. Pat. No. 4,075,407 discloses phosphorane intermediates represented by the formula:

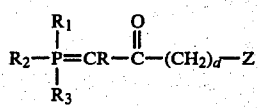

wherein R, $R_1$, $R_2$ and $R_3$ are as defined above, d is 3,4 or 5 and Z is halo.

I have now found that the synthesis of the analgesic agents of U.S. Pat. No. 4,075,407 is greatly facilitated by employing the hydroxy-substituted phosphoranes and salts thereof of the present invention in place of the intermediates disclosed in U.S. Pat. No. 4,075,407.

SUMMARY OF THE INVENTION

The present invention relates to hydroxy-substituted phosphoranes and salts thereof which are useful as intermediates in the preparation of the heterocyclic phosphonium salts disclosed in U.S. Pat. No. 4,075,407, and to improved methods of producing said phosphonium salts.

The intermediates of this invention are represented by Formulae I and II:

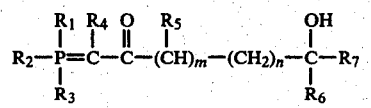

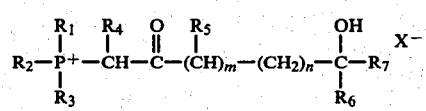

wherein $R_1$, $R_2$ and $R_3$ are the same or different members of the group consisting of lower alkyl, $C_5$–$C_6$ cycloalkyl, and

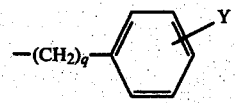

wherein q is an integer from 0 to 4 and Y is selected from the group consisting of hydrogen, halogen, lower alkyl and lower alkoxy; $R_4$ can be hydrogen or $C_1$–$C_3$ straight or branched chain alkyl; the sum of $n+m=3$–$5$; $R_5$ is hydrogen or lower alkyl; $R_6$ and $R_7$ are the same or different members of the group consisting of hydrogen, lower alkyl, and

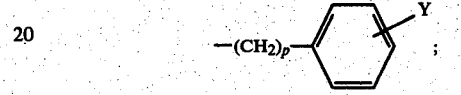

p is an integer of 0 or 1; and X is an anion.

The compounds are useful as intermediates for the heterocyclic phosphonium salts disclosed and claimed in U.S. Pat. No. 4,075,407. An improved process for preparing the phosphonium salts of U.S. Pat. No. 4,075,407 is also provided by the present invention.

The term "lower alkyl" includes both straight and branched chain alkyl radicals having from 1 to 6 carbon atoms such as methyl, ethyl, n-propyl, iso-propyl, n-butyl, iso-butyl, tert-butyl, n-pentyl, 2-methyl-butyl, 2,2-dimethylpropyl, n-hexyl, etc.

The cycloalkyl radicals containing 5 and 6 carbon atoms are cyclopentyl and cyclohexyl, respectively.

Representative alkoxy groups containing from 1 to 6 carbon atoms include methoxy, ethoxy, propoxy, butoxy, etc. and the corresponding branched-chain radicals, e.g., iso-propoxy.

The term "anions" includes, but is not limited to chloride, bromide, iodide, fluoride, acetate, propionate, sulfate, bisulfate, acetate, oxalate, valerate, oleate, laurate, borate, citrate, maleate, fumarate, lactate, succinate, tartrate, benzoate, tetrafluoroborate, trifluoromethyl sulfonate, napsylate, tosylate, etc. Since the compounds of this invention are used as intermediates in organic syntheses, the anion need not be limited to a pharmaceutically acceptable anion, i.e. a non-toxic anion.

DETAILED DESCRIPTION OF PREFERRED EMBODIMENTS

The hydroxy substituted phosphoranes and salts thereof can be conveniently prepared by reaction of a phosphonium ylide represented by the formula:

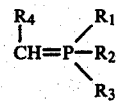

with a hydroxyalkanoic acid lactone in an aprotic medium with or without a dipolar aprotic solvent.

Thus the present invention also provides a new and unique method of preparing hydroxy-substituted phosphoranes as well as the novel compounds. The lactones and their methods of preparation are familiar to one skilled in the art and are described by, for example, Starcher and Phillips, J. Am. Chem. Soc., 80, 4079 (1958) and by House, "Modern Synthetic Reactions," p. 323, 2nd Ed., W. A. Benjamin Inc., Melano Park, Calif. (1972). The hydroxy phophoranes or their salts may also be obtained, if desired, by hydrolysis of the hetrocyclic phosphonium salts of U.S. Pat. No. 4,075,407.

The hydroxy phosphoranes or phosphonium salts are converted into the heterocyclic phosphonium salts by treatment with a protic or Lewis acid. Alternatively, treatment with concentrated acid gives the halophosphonium salts of U.S. Pat. No. 4,075,407 and thus the analgesic hetrocyclic phosphonium salts by the methods described therein. The hydroxy phosphonium salts and the hydroxyphosphoranes are readily converted one into the other by treatment with a base or acid respectively and for purposes of conversion to the analgesic agents are equivalent. Conveniently, excess phosphonium ylide can serve as the base during the initial lactone reaction. The process is outlined below:

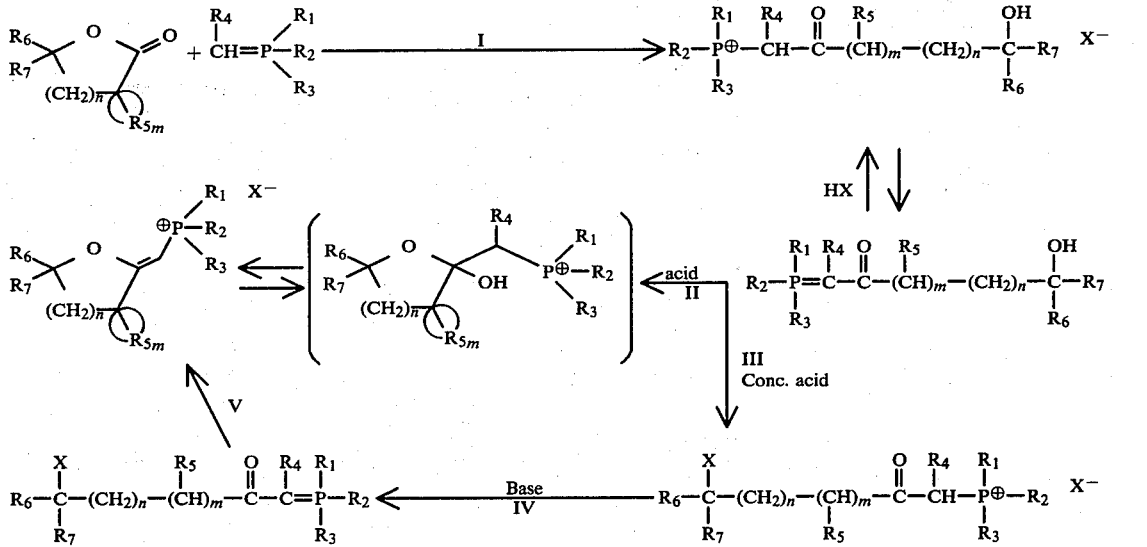

In the foregoing reaction schemes, Steps I→II and I→III represent the new, improved and greatly simplified processes provided by one aspect of the present invention. Steps IV→V are part of the process of U.S. Pat. No. 4,075,407.

The processes of the present invention have a number of advantages over the processes of U.S. Pat. No. 4,075,407. The processes of the present invention are greatly simplified over the prior art process and require only two steps. Further, the present processes eliminates the use of explosive reagents. Another advantage of the present processes lies in the final step, an acid catalyzed cyclization or elimination rather than the prior art $SN_2$ reaction which allows a wider choice of bulky substituents. And finally, the intermediates obtained from step I can be converted to the halophosphoranes of U.S. Pat. No. 4,075,407, if desired.

The simplicity of the present processes cannot be overemphasized. No special reaction conditions, i.e., temperature, pressure, etc. are required. The only modifications are dependent on the acid used. The acid can be either a Lewis acid such as triethyloxonium tetrafluoroborate, triethyl oxoniumhexafluorophosphate, trimethyloxoniumhexachloroantiminate, etc., or a protic acid. The protic acids used in the practice of the present invention are acids such as hydrochloric, hydrobromic, hydroiodic, sulfuric, toluenesulfonic, trifluouromethanesulfonic, trifluoroacetic acid, etc.

In the case of a Lewis acid, the acid is reacted with a phosphorane of Formula I or a phosphonium salt of Formula II under aprotic conditions in the presence of a suitable solvent such as methylene chloride, chloroform, tetrafluoroethane, etc. In the case of a protic acid, the acid is first diluted with an organic solvent such as ethanol, methanol, isopropanol, dimethylsulfoxide, etc., prior to reaction with a compound of Formula I or Formula II.

In some cases it may be advantageous to add a water scavenging agent such as trimethylorthoformate or molecular sieves such as Linde, Division of Union Carbide, 3A molecular sieve.

The following examples illustrate the present invention.

EXAMPLE 1

Preparation of (5-hydroxy-2-oxopentyl)triphenylphosphorane

Methyltriphenyl phosphonium bromide (71 g, 0.2 M), obtained from Aldrich Chemical Co., Milwaukee, Wis., was suspended in tetrahydrofuran (500 ml) with stirring under an argon atmosphere. The suspension was cooled to approximately −78° C. in a dry ice-acetone bath, and phenyl lithium (110 ml, 1.87 M) was added dropwise over a period of about 1 hour. When the addition was complete, the solution was allowed to warm to room temperature overnight. Dimethylsulfoxide was added until all solids had dissolved and the reaction mixture was clear. The solution was stirred at room temperature, cooled to approximately 10° C. and butyrolacetone (10 ml) was added thereto in one portion and stirred at room temperature for 5 hours. The latter reaction mixture was poured into water (1 liter), stirred vigorously for one half hour and extracted four times with benzene. The benzene extracts were combined, washed 3 times with 250 ml portions of water, twice with 250 ml portions of saturated sodium chloride solution, and dried over sodium sulfate. Partial removal of solvent gave 42.4 g of product. Recrystallization from benzene/cyclohexane resulted in pure (5-hydroxy-2-oxopentyl)triphenylphosphorane, m.p. 146°–147° C.; PMR (CDCl₃) δ1.83 (2H,m), 2.4 (2H,m), 3.66 (2H,m), 3.76 (1H,d,J=27Hz), 7.6 (15H,m) and having the following structure

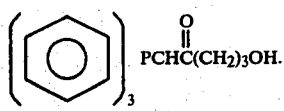

EXAMPLE 1A

Preparation of (5-hydroxy-2-oxopentyl)triphenylphosphorane Alternate Process

Several small pieces of sodium (about 1 g) were added to 250 ml liquid ammonia cooled to −50° C. via a dry ice - isopropanol bath under an argon atmosphere. Ferric chloride (0.1 g) was added as a catalyst and the mixture stirred for 1 hour. The remaining sodium (5 g) was then added in small pieces over the next 45 minutes. After stirring for 7 hours, the dry ice - isopropanol bath was removed and 250 ml of tetrahydrofuran was added slowly. Upon warming to room temperature the excess ammonia evaporated leaving a grey suspension of NaNH₂ (0.26 moles) in tetrahydrofuran.

To the above rapidly stirring suspension of NaNH₂ (0.26 moles) in tetrahydrofuran under an argon atmosphere was added methyl triphenylphosphonium bromide (75 g, 0.21 moles) in small portions over 30 minutes. The above mixture was stirred for 64 hours and the resulting orange solution was heated to reflux for 2 hours and filtered hot through celite (under argon). The filter cake was washed with 50 ml of hot tetrahydrofuran and combined with the filtrate.

γ-Butyrolactone (75 ml) was added dropwise over 30 minutes to an ice cooled solution of the above-prepared phosphorane in 300 ml of tetrahydrofuran. The ice bath was removed and the reaction was stirred overnight. The solution was poured into 1500 ml cold water and stirred for 64 hours. The resulting white solid was filtered off under reduced pressure, washed with 50 ml toluene and dissolved in 150 ml methylene chloride. After drying over sodium sulfate for 1 hour the solution was filtered and the volume was reduced to 75 ml by a nitrogen flush. Ethyl ether (50 ml) was added and the solution was placed in the refrigerator where a white solid was filtered off under reduced pressure and washed with 100 ml ethyl ether to yield 26.0 g product. The filtrate was reduced to 100 ml volume (nitrogen flush) and placed in the refrigerator. A second crop of product was filtered off and washed with 50 ml of ethyl ether. Both crops of product were identical to the product of Example 1.

EXAMPLE 2

Preparation of (6-hydroxy-2-oxohexyl)triphenylphosphorane

Following the method of Example 1, methyl triphenyl phosphonium bromide (7.14 g), tetrahydrofuran (100 ml); phenyl lithium (11 ml of 1.87 M), dimethylsulfoxide (75 ml) and γ-valerolactone (0.8 ml) were reacted to produce 1.18 g of (6-hydroxy-2-oxohexyl)triphenylphosphorane; m.p. 121°–124° C.; PMR (CDCl₃) δ1.65 (4H,m), 2.35 (2H,m), 3.32 (2H, broad), 3.57 (2H,t,J=6Hz), 7.5 (15H,m), and having the following structure:

EXAMPLE 3

Preparation of (5-hydroxy-2-oxo-5-phenylpentyl)triphenylphosphorane

Following the method of Example 1, methyltriphenylphosphonium bromide (22 g), tetrahydrofuran (200 ml), phenyl lithium (35 ml, 1.87 M) dimethylsulfoxide and 4-phenyl-butyrolactone (5 g) were reacted to yield 8 g of crude product. Column chromatography on 250 g of silica, packed and eluted with ethyl acetate-benzene [5:50 (v/v)] resulted in pure product: PMR (CDCl₃) δ2.05 (2H,m), 2.6 (2H,m), 3.8 (1H,d,J=27Hz), 4.8 (1H,t,J=6.5Hz), 7.5 (20H,m) and having the formula

EXAMPLE 4

Preparation of (5-hydroxy-2-oxohexyl)triphenylphosphorane

Following the method of Example 1, methyltriphenylphosphonium bromide (22 g), tetrahydrofuran (200 ml) phenyl lithium (35 ml, 1.87 M), dimethylsulfoxide and 4-methylbutyrolactone (5.8 ml) were reacted to yield 15 g of crude product. Column chromatography of the latter of Silica packed and eluted with four percent ethanol-methylene chloride, yielded 6.89 g of (5-hydroxy-2-oxohexyl)triphenylphosphorane: PMR (CDCl₃) δ1.18 (3H,d,J=6Hz), 1.8 (2H,m), 2.55 (2H,m), 3.85 (2H,m), 7.5 (15H,m); and having the formula

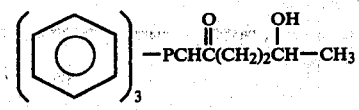

EXAMPLE 5

Preparation of (5-hydroxy-1-methyl-2-oxopentyl)triphenylphosphorane

Following the method of Example 1, with the exception of a 36 hour reaction period, 3.71 g of ethyltriphenylphosphonium bromide, 200 ml of tetrahydrofuran, 67 ml of 1.5 N phenyl lithium, 200 ml of dimethylsulfoxide and 3.8 ml of γ-buyrolactone gave 20 g of crude product. The latter was chromatographed on silica to yield 6.4 g of desired product upon elution with ethanol: Mass spectrum [M+ =376]; PMR (CDCl₃)δ1.63 (3H,d,J - 16 Hz), 1.83 (2H,m), 2.58

(2H,m), 3.65 (2H,t,J=5.5Hz) and 7.67 (15H,m); and having the formula

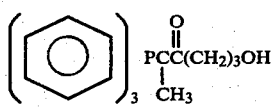

EXAMPLE 6

Preparation of [5-hydroxy-5-(4-fluorophenyl)-2-oxopentyl]-triphenylphosphorane

Following the method of Example 1, 22 g of methyltriphenyl phosphonium bromide, 25 ml of 1.87 M phenyl lithium, 200 ml of tetrahydrofuran, dimethylsulfoxide and 5.5 g of 4-(p-fluorophenyl)-butyrolacetone gave 15 g of impure product which was chromatographed on 300 g of silica to give 2.6 g of product having the formula

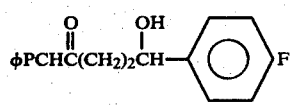

EXAMPLE 7

Preparation of [2-oxo-(2-hydroxymethylphenyl)ethyl]-triphenylphosphorane

Following the method of Example 1, 22 g of methyltriphenylphosphonium bromide, 200 ml of tetrahydrofuran, 35 ml of 1.87 M phenyl lithium, dimethylsulfoxide and 4.22 g of phthalide were reacted, and the resulting crude product was chromatographed on 400 g of silica packed and eluted with 30 percent ethyl acetate-methylene chloride to yield 5.4 g of product having the formula

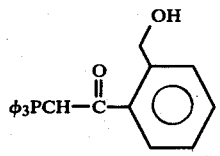

EXAMPLE 8

Preparation of (5-hydroxy-3-methyl-2-oxopentyl)-triphenylphosphorane

Following the method of Example 1, except for a 20 hour reaction period, 17.8 g of methyltriphenylphosphonium bromide, 150 ml of tetrahydrofuran, 30 ml of 1.87 M phenyl lithium, dimethylsulfoxide and 4 ml of α-methylbutyrolactone were reacted. Chromatography on approximately 300 g of silica and elution with ethyl acetate resulted in 2.3 g of product: PMR (CDCl$_3$)δ1.22 (3H,d,J=7Hz), 2.78 (2H,m), 2.6 (1H,m), 3.67 (2H,t,J=5.5Hz), 4.4 (2H,s), 7.5 (15H,m).

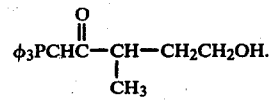

EXAMPLE 9

Preparation of (5-hydroxy-1-methyl-2-oxopentyl-5-phenylpentyl)triphenylphosphorane Following the method of Example 8, 37 g of ethylphenylphosphonium bromide, 200 ml of tetrahydrofuran, 67 ml of 1.5 M phenyl lithium, about 200 ml of dimethylsulfoxide and 8.1 g of 4-phenylbutyrolacetone yielded 13.2 g of product following column chromatography on 450 g of silica and elution with ethanol: PMR (CDCL$_3$)δ 1.59 (3H,d,J=16Hz), 2.1 (2H,m), 2.65 (2H,m), 4.74 (1H,t,J=5.5 Hz), 7.5 (20H,m).

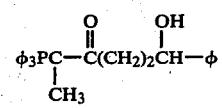

EXAMPLE 10

Preparation of (5-hydroxy-2-oxopentyl)triphenylphosphonium chloride and (5-hydroxy-5-oxopentyl)triphosphorane 20 g of triphenyl[(tetrahydrofuran-2-ylidene)methyl] phosphonium chloride was dissolved in 150 ml of 10% aqueous hydrochloric acid and allowed to stand at room temperature for 19 days. Extraction with methylene chloride and drying over sodium sulfate gave 2.65 g of crude (5-hydroxy-2-oxopentyl)triphosphonium chloride. This material was dissolved in water, made basic with potassium carbonate and the resulting crystals filtered to give 2.04 g of (5-hydroxy-2-oxopentyl)-triphosphorane after drying overnight at 50° C. at 0.5 mm pressure, identical with that prepared by the method of Example 1.

EXAMPLE 11

Preparation of (6-hydroxy-2-oxohexyl)triphenyl phosphonium chloride and (6-hydroxy-2-oxohexyl)triphenylphosphorane 3.95 g of triphenyl[tetrahydro-2H-pyran-2-ylidene)-methyl]phosphonium chloride was dissolved in 150 ml of methanol and 9 ml of concentrated hydrochloric acid added. The reaction mixture was refluxed for about 2 days, followed by standing at room temperature for 2 days. The solution was diluted with 400 ml of water, extracted with ether and then methylene chloride. Sodium chloride was added and the solution was extracted with 3 50 ml portions of methylene chloride. The final methylene chloride extracts were combined, dried over sodium sulfate, the solvent removed under nitrogen gas and the residue dried 3 hours at 50° C. under 0.5 mm pressure to give 2 g of (6-hydroxy-2-oxyhexyl)triphenylphosphorane identical with that obtained by the process of Example 2.

EXAMPLE 12

Preparation of triphenyl[(tetrahydro-5-methyl-furan-2-ylidene)methyl]phosphonium tetrafluoroborate 1.5 g of (5-hydroxy-2-oxopentyl)triphenylphosphorane was dissolved in 20 ml of methylene chloride under a nitrogen atmosphere, cooled in dry ice/acetone bath and 15 ml of triethyloxonium tetrafluoroborate as a 1 M solution in methylene chloride was added. The reaction mixture was stirred at about −78° C. for 0.5 hour and allowed to warm to room temperature over about 2 hours, decanted into ice water and stirred vigorously with the addition of an additional 30 ml of methylene chloride. The extraction was repeated twice, the extracts combined, dried over sodium sulfate, the solvent removed under nitrogen gas followed by warming to 40° C. for 2 hours at 0.5 mm. Crystallization from ethyl acetate gave 700 mg of the desired product, m.p. 118.5°–122.5° C.

EXAMPLE 13

Preparation of [(tetrahydro-2H-furan-2-ylidene)-methyl]triphenylphosphonium chloride 2.5 g of (5-hydroxy-2-oxopentyl)triphenylphosphorane was dissolved in concentrated hydrochloric acid and heated at reflux for 20 hours when an additional 50 ml of concentrated hydrochloric acid was added and heating continued for 24 hours. The solvent was removed at 60° C. with a rotary evaporator and the oil remaining treated with excess potassium carbonate, extracted with benzene four times, and the extracts were combined and dried over sodium sulfate. After filtration, the solution was heated at reflux for 18 hours to yield 1.5 g of [(tetrahydro-2H-furan-2-ylidene)methyl]triphenylphosphonium chloride having the structure.

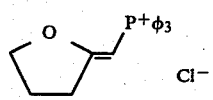

EXAMPLE 14

Alternate preparation of (5-hydroxy-2-oxopentyl)triphenylphosphonium chloride 2.3 g of (5-hydroxy-2-oxopentyl)triphenylphosphorane was dissolved in methylene chloride and extracted 4 times with aqueous hydrochloric acid (pH 1 to 2) and the extracts were combined, sodium chloride added and then extracted with methylene chloride (4×50 ml). The organic extracts were combined, dried over sodium sulfate, and the solvent removed under nitrogen gas followed by heating to 50° C./0.5 mm Hg for 6 hours and crystallization from acetone to give 1.9 g of product, m.p. 143°–145° C. identical with that obtained by the process in Example 10.

EXAMPLE 15

Alternate preparation of [(tetrahydro-2H-furan-2-ylidene)-methyl]triphenylphosphonium chloride 3.0 g of (5-hydroxy-2-oxypentyl)triphenylphosphorane was dissolved in 112 ml of methanol and 6.75 ml of concentrated hydrochloric acid was added and the solution stirred at a gentle reflux for 3 days. The solvents were removed under reduced pressure on a rotary evaporator to yield crystalline product m.p. 231°–232° C., 2.1 g, after recrystallization from acetone.

EXAMPLES 16–18

The following compounds are prepared by the method of Example 1, substituting the appropriate phosphonium ylide for methyltriphenyl phosphonium bromide.

(5-Hydroxy-2-oxopentyl)tri-n-butylphosphorane from methyl tri-n-butyl phosphonium tetrafluoroborate.

(5-Hydroxy-2-oxopentyl)trimethylphosphorane from tetramethylphosphonium iodide.

(5-Hydroxy-2-oxopentyl)tri-n-hexylphosphorane from methyl tri-n-hexylphosphonium bromide.

EXAMPLE 19

Following the method of Example 9, (5-hydroxy-1-methyl-2-oxopentyl-5-phenylpentyl)tricyclopentylphosphonium trifluoroacetate was prepared from methyl tricyclopentylphosphonium trifluoroacetate.

EXAMPLE 20

Following the method of Example 1, (5-hydroxy-2-oxopentyl)cyclohexyldiphenyl phosphonium bromide is prepared from cyclohexyldiphenylmethylphosphonium bromide.

EXAMPLE 21-25

Following the method of Example 10, the following compounds were prepared:

(6-Hydroxy-2-oxopentyl)tri-n-butylphosphonium chloride, m.p. 109°–112° C. from [(tetrahydro-2H-pyran-2-ylidene)methyl]-tri-n-butylphosphonium chloride.

(6-Hydroxy-2-oxohexyl)tri-(4-methoxyphenyl)phosphonium chloride, m.p. 178°–181° C. from a mixture of [(tetrahydro-2H-pyran-2-ylidene)methyl]tri-(4-methoxyphenyl)phosphonium chloride and [(5,6-dihydropyran-2-yl)methyl]tri-(4-methoxyphenyl)phosphonium chloride (U.S. Pat. No. 4,075,407).

(7-Hydroxy-2-oxoheptyl)triphenylphosphonium bromide, m.p. 156°–159° C. from [(2-oxopanylidene)methyl]triphenylphosphonium bromide.

(7-Hydroxy-2-oxoheptyl)triphenylphosphorane, m.p. 138°–141° C. from (7-hydroxy-2-oxoheptyl)triphenylphosphonium bromide.

(5-Hydroxy-1-methyl-2-oxohexyl)-triphenylphosphonium chloride, m.p. 172°–174° C. from [1-(tetrahydro-2H-pyran-2-ylidene)-ethyl]-triphenylphosphonium chloride.

I claim:
1. A compound represented by the formulae:

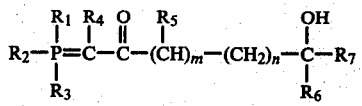

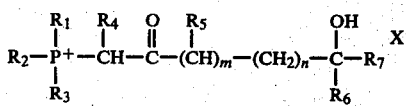

wherein $R_1$, $R_2$ and $R_3$ are the same or different members of the group consisting of lower alkyl, $C_5$–$C_6$ cycloalkyl, and

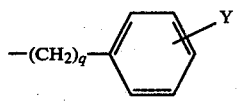

wherein q is an integer from 0 to 4 and Y is selected from the group consisting of hydrogen, halogen, lower alkyl and lower alkoxy; $R_4$ can be hydrogen or $C_1$–$C_3$ straight or branched chain alkyl; the sum of $n+m=2-6$; $R_5$ is hydrogen or lower alkyl; $R_6$ and $R_7$ are the same or different members of the group consisting of hydrogen, lower alkyl, and

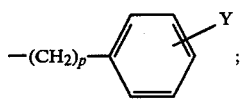;

p is an integer of 0 or 1; and X is an anion.

2. A compound of claim 1 represented by the formula

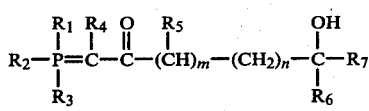  I wherein $R_1$, $R_2$ and $R_3$ are the same or different members of the group consisting of lower alkyl, $C_5$–$C_6$ cycloalkyl, and

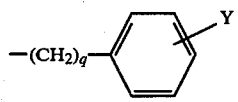

wherein q is an integer from 0 to 4 and Y is selected from the group consisting of hydrogen, halogen, lower alkyl and lower alkoxy; $R_4$ can be hydrogen or $C_1$–$C_3$ straight or branched chain alkyl; the sum of $n+m=2-6$; $R_5$ is hydrogen or lower alkyl; $R_6$ and $R_7$ are the same or different members of the group consisting of hydrogen, lower alkyl, and

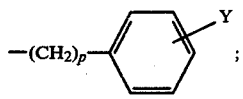;

p is an integer of 0 or 1; and X is an anion.

3. A compound of claim 1 or 2 wherein q is 0.
4. A compound of claim 3 wherein $R_1$, $R_2$ and $R_3$ each are phenyl.
5. A compound of claim 4: (5-hydroxy-2-oxopentyl)-triphenylphosphorane.
6. A compound of claim 4: (6-hydroxy-2-oxohexyl)-triphenylphosphorane.
7. A compound of claim 4: (5-hydroxy-3-methyl-2-oxopentyl)triphenylphosphorane.
8. A compound of claim 4: (5-hydroxy-1-methyl-2-oxopentyl)triphenylphosphorane.
9. A compound of claim 4: (5-hydroxy-2-oxohexyl)-triphenylphosphorane.
10. A compound of claim 2 wherein q is 0 and $R_6$ and $R_7$ are

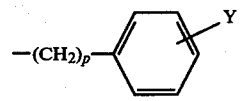

11. A compound of claim 10: [2-oxo-(2-hydroxymethylphenyl)ethyl]triphenylphosphorane.
12. A compound of claim 10: [5-hydroxy-5-(4-fluorophenyl)-2-oxopentyl]triphenylphosphorane.
13. A compound of claim 10: (5-hydroxy-1-methyl-2-oxo-5-phenylpentyl)triphenylphosphorane.
14. A compound of claim 10: (5-hydroxy-2-oxo-5-phenylpentyl)triphenylphosphorane.
15. A compound of claim 1 represented by the formula

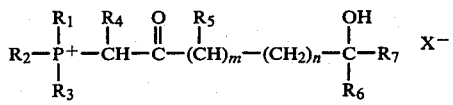

wherein $R_1$, $R_2$ and $R_3$ are the same or different members of the group consisting of lower alkyl, $C_5$–$C_6$ cycloalkyl, and

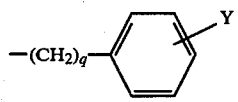

wherein q is an integer from 0 to 4 and Y is selected from the group consisting of hydrogen, halogen, lower alkyl and lower alkoxy; $R_4$ can be hydrogen or $C_1$–$C_3$ straight or branched chain alkyl; the sum of $n+m=2-6$; $R_5$ is hydrogen or lower alkyl; $R_6$ and $R_7$ are the same or different members of the group consisting of hydrogen, lower alkyl, and

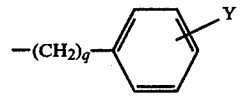;

p is an integer of 0 or 1; and X is an anion.

16. A compound of claim 15 wherein $R_1$, $R_2$ and $R_3$ each are phenyl.
17. A compound of claim 16 wherein q is 0.
18. A compound of claim 17: (5-hydroxy-2-oxopentyl)triphenylphosphonium chloride.
19. A compound of claim 17: (6-hydroxy-2-oxopentyl)tri-n-butylphosphonium chloride.
20. A compound of claim 17: (6-hydroxy-2-oxohexyl)tri-(4-methoxyphenyl)phosphonium chloride.
21. A compound of claim 17: (7-hydroxy-2-oxoheptyl)triphenylphosphonium bromide.
22. A compound of claim 17: (7-hydroxy-2-oxoheptyl)triphenylphosphorane.
23. A compound of claim 17: (5-hydroxy-1-methyl-2-oxohexyl)triphenylphosphonium chloride.
24. A compound of claim 1 where $R_1$, $R_2$ and $R_3$ each are $C_1$–$C_6$ alkyl.

25. A compound of claim 1 wherein one of $R_1$, $R_2$ and $R_3$ is $C_5$–$C_6$ cycloalkyl.
26. A compound of claim 1 wherein two of $R_1$, $R_2$ and $R_3$ are
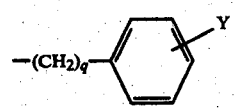
* * * * *